(12) United States Patent  
Cooper

(10) Patent No.: US 6,562,044 B1
(45) Date of Patent: *May 13, 2003

(54) SOFT TISSUE FIXATION DEVICE

(75) Inventor: Daniel E. Cooper, 2909 Lemmon Ave., Dallas, TX (US) 75204-2385

(73) Assignee: Daniel E. Cooper, Dallas, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 178 days.

(21) Appl. No.: 09/643,010

(22) Filed: Aug. 21, 2000

(51) Int. Cl.[7] ................................................ A61B 17/56
(52) U.S. Cl. ........................ 606/72; 606/73; 623/13.11
(58) Field of Search ............................ 606/60, 72, 73, 606/151, 232, 104; 623/13.11, 13.12

(56) References Cited

U.S. PATENT DOCUMENTS

| 4,988,351 | A | 1/1991 | Paulos et al. ............... 606/72 |
| 5,116,337 | A | 5/1992 | Johnson ....................... 606/73 |
| 5,147,362 | A | 9/1992 | Goble .......................... 606/72 |
| 5,152,790 | A | 10/1992 | Rosenberg et al. ........... 623/13 |
| 5,266,075 | A | 11/1993 | Clark et al. .................. 623/15 |
| 5,282,802 | A | 2/1994 | Mahony, III ................. 606/72 |
| 5,496,326 | A | 3/1996 | Johnson ....................... 606/88 |
| 5,562,668 | A | 10/1996 | Johnson ....................... 606/72 |
| 5,674,224 | A | 10/1997 | Howell et al. ................ 606/88 |
| 5,871,504 | A | 2/1999 | Eaton et al. ................ 606/232 |
| 5,931,869 | A | 8/1999 | Boucher et al. .............. 623/13 |
| 5,941,901 | A | 8/1999 | Egan .......................... 606/232 |
| 6,379,361 | B1 * | 4/2002 | Beck, Jr. et al. ............. 606/72 |

* cited by examiner

Primary Examiner—David O. Reip
(74) Attorney, Agent, or Firm—Haynes & Boone, LLP

(57) ABSTRACT

Method and apparatus are described for a soft tissue fixation device for being biased between a soft tissue graft and an interference screw in a bone tunnel. The device has a contoured body portion having an inner surface and an outer surface. A plurality of spikes protrude from the outer surface of the body portion, the spikes extending perpendicular to the longitudinal axis of the body portion and parallel to each other. The distal ends of the spikes define a flat plane. A pin axially extends from the body portion for receiving a portion of the graft.

22 Claims, 5 Drawing Sheets

SOFT TISSUE FIXATION DEVICE

BACKGROUND

This disclosure relates generally to a device to be implanted during orthopedic surgery, and more particularly, to a soft tissue fixation device.

Reconstructive surgery may be required after a patient injures a ligament, for example, the anterior cruciate ligament (ACL) of the knee joint. In ACL reconstruction, a replacement soft tissue or ligament ("graft" generically) is often used. The graft is affixed to a bone of the patient, such as the femur or tibia, to secure the graft while the graft attaches to the bone. In one method of affixing a graft to a bone, a tunnel is drilled through the bone, and a portion of the graft is inserted into the tunnel. A mechanical fastener, such as an interference screw and wedge, may then be inserted into the tunnel, thus holding the graft in the desired position.

However, such prior art fasteners are prone to allow slippage of the graft ("graft slippage") for a variety of reasons, resulting in undesirable loss of tension on the graft. Graft slippage is a very serious problem, impairing the efficacy of the reconstruction procedure, and in some cases even necessitating a second surgery to reposition and tension the graft. Moreover, during installation, sharp edges on the wedge or screw can cut or fray the graft, sometimes damaging the graft beyond usefulness. Also, it is sometimes difficult to judge the length of graft inserted into the bone tunnel, thus, too little of the graft may be engaged by the mechanical fastener, resulting in graft slippage.

Therefore, what is needed is a device to securely affix a graft to a bone. Moreover, the device should be contoured to prevent damage to the graft. Finally, the device should allow a surgeon to readily estimate the length of graft inserted into the bone tunnel.

SUMMARY

Accordingly, an embodiment of the present invention provides for a soft tissue fixation device for being biased between a soft tissue graft and an interference screw in a bone tunnel. The device has a contoured body portion having an inner surface and an outer surface. A plurality of spikes protrude from the outer surface of the body portion, the spikes extending perpendicular to the longitudinal axis of the body portion and parallel to each other. The distal ends of the spikes define a flat plane. A pin axially extends from the body portion for receiving a portion of the graft.

The device may be used in any procedure where a soft tissue or ligament graft needs to be directly affixed to a bone, such as knee ligament reconstruction, or other soft tissue reconstructions used in orthopedic surgery. One advantage of the embodiments described herein is they each securely affix the graft to the bone. Also, the embodiments are contoured to prevent damage to the graft. Finally, the embodiments allow a surgeon to readily adjust the length of graft inserted into the bone tunnel, thus improving the ability to properly tension the graft at the time of initial fixation.

DETAILED DESCRIPTION

Figure 1:
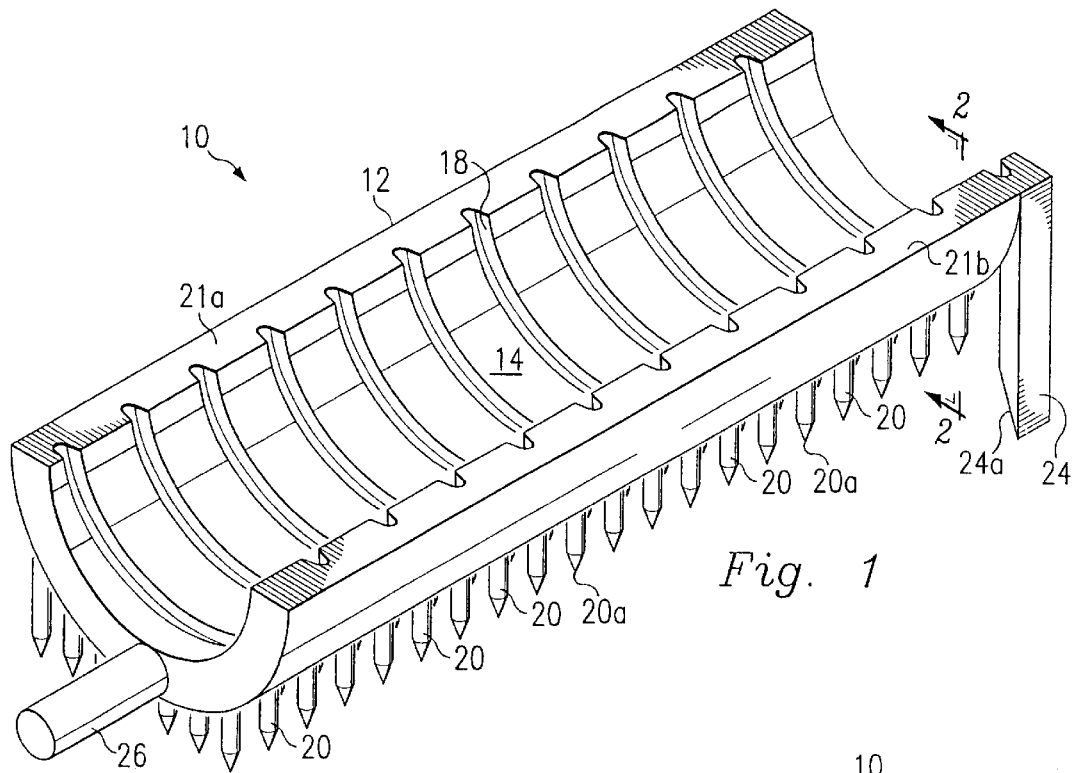
FIG. 1 is a perspective view of a soft tissue fixation device according to one embodiment of the present invention for use in a patient.
Figure 2:
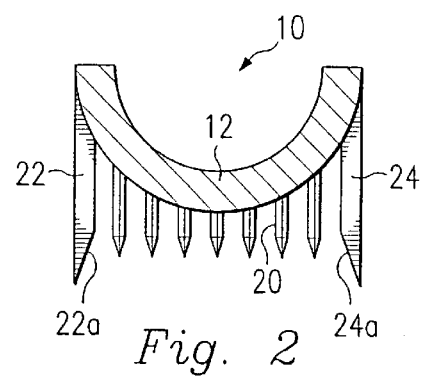
FIG. 2 is a cross sectional view of the device of FIG. 1.

Referring to FIGS. 1–5B, the reference numeral 10 refers to a soft tissue fixation device according to one embodiment of the present invention. The device 10 has a semi-cylindrical body portion 12, which is substantially U-shaped in cross-section (FIG. 2). The body portion 12 has an inner surface 14 and an outer surface 16.

A series of channels, or grooves, 18 are orthogonally disposed along the inner surface 14 of the body portion 12, for reasons to described.

Figure 3:
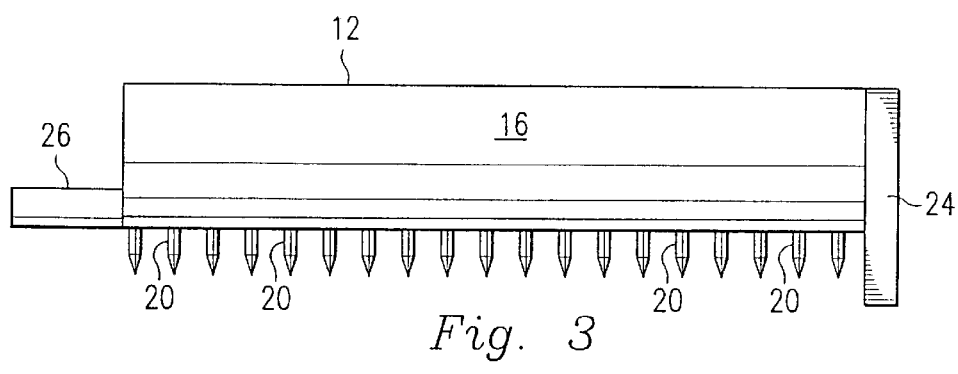
FIG. 3 is a side plan view of the device of FIG. 1.

A plurality of spikes 20 protrude from the outer surface 16 of the body portion 12. The spikes 20 extend perpendicular to the longitudinal axis of the body portion 12, and parallel to each other. As depicted, the spikes are arranged in longitudinal rows (FIG. 2), as well as lateral rows (FIG. 3). However, the disclosure contemplates staggered arrangements of the spikes 20 as well.

The distal ends 20a of the spikes 20 define a flat plane extending parallel to an imaginary plane extending between the uppermost surfaces 21a–b of the body portion 12. It is understood that in order to define the flat plane, the length of each of the respective spikes 20 is predetermined based upon the spike's relative location on the contoured outer surface 16 of the body portion 12. The distal ends 20a of the spikes 20 may be sharpened, as depicted, or rounded, for reasons to be described.

A pair of spurs 22–24 project from a distal end of the body portion 12 in an orientation parallel to the spikes 20. The spurs 22–24 extend past the flat plane defined by the spike ends 20a, and terminate in chisel-shaped ends 22a–24a, respectively.

A pin 26 extends axially from the opposite end of the body portion 12, relative to the spurs 22–24. The pin 26 is oriented parallel to the longitudinal axis of the body portion 12, and has a substantially cylindrical shape. The length of the device 10 may be measured from the distal end of the pin 26 to the trailing edge of the spurs 22–24.

Figure 4:
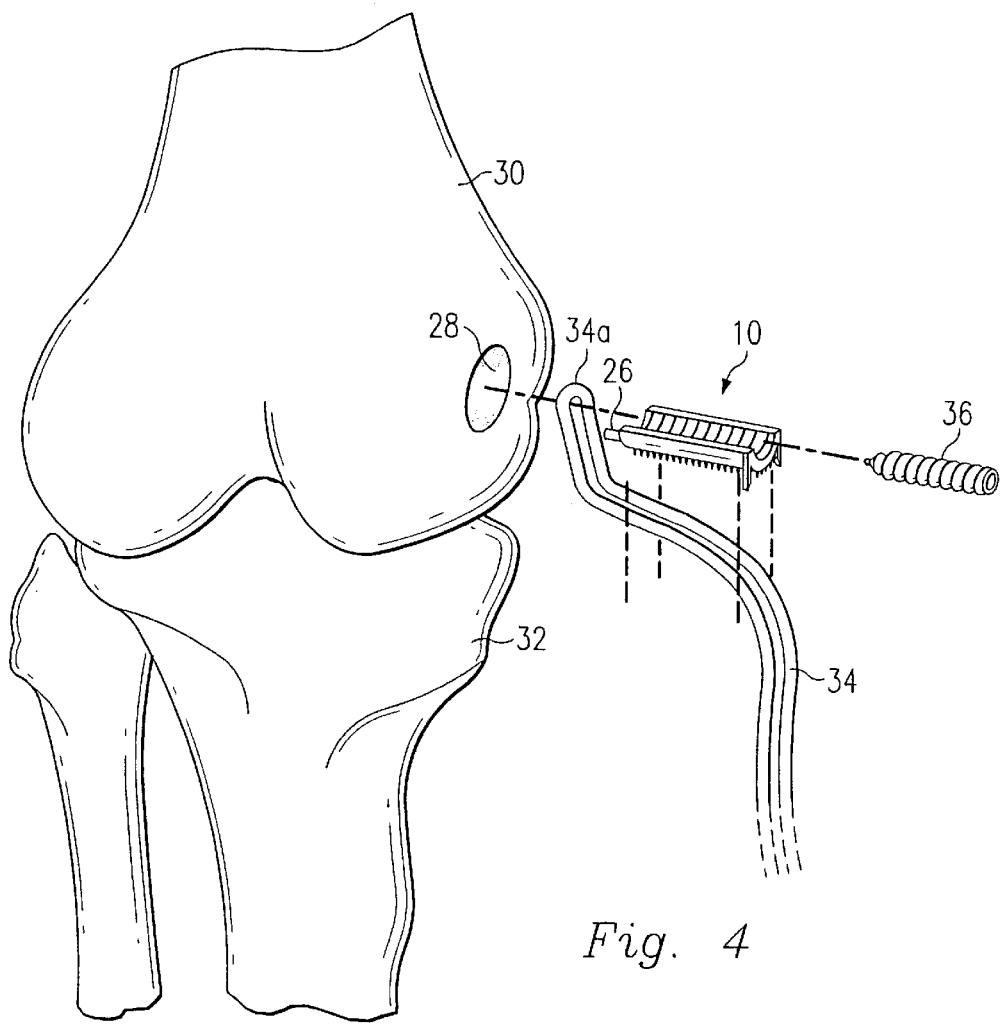
FIG. 4 is a perspective view of the device of FIG. 1 being placed in a patient.

In operation, and referring to FIG. 4, a bone tunnel 28 is bored in a patient's femur (hereinafter "bone") 30 by any conventional means. It is understood that the bone tunnel alternatively could be bored in the patient's tibia 32. In the preferred method of use, the bone tunnel 28 is bored at a right angle relative to the longitudinal axis of the bone 30. Thus, once the device 10 is secured in the bone tunnel 28, the major component of any force that would tend to create graft slippage occurs at a right angle to the device, along the bone's longitudinal axis. The resulting force vector is thus considerably diminished, and thereby far less likely to result in graft slippage. However, the angle of the bone tunnel 28 is not a critical feature. The bone tunnel 28 should be of a depth slightly greater than the length of the soft tissue fixation device 10.

A graft 34 to be affixed to the bone 30 is bent over itself to form a loop 34a. The graft loop 34a is placed over the pin 26, and the trailing ends of the graft threaded between the spurs 22–24. The spurs 22–24 help direct the graft 34 under the spikes 20 to better engage the graft, and to prevent the edges of the device 10 from cutting the graft. Also, the outer surface 16 of the body portion is contoured to reduce the chance of the edges of the device cutting the graft 34.

The device 10, and hence the graft 34, is inserted into the bone tunnel 28. It is understood that once the loop 34a is placed over the pin 26, the length of the device 10 inserted in the bone tunnel 28 corresponds directly with the length of graft 34 inserted into the bone tunnel. This feature allows a surgeon to readily adjust the length of graft inserted into the bone tunnel.

Once installed, if the resulting tension on the graft 34 is determined to be less than optimal for the reconstruction procedure, the graft and device 10 may be removed from the bone tunnel 28, and the graft loop 34a re-formed in a position corresponding to producing greater or lesser graft tension, as desired. Thus, the graft tension may be easily adjusted to produce an optimal graft tension, a significant advantage.

Once proper graft tension has been achieved, an interference screw 36, having threads 36a, is inserted in the bone tunnel 28 above the device 10. The screw 36 thus engages the inner surface 14 of the body portion 12. The screw 36 may be rotated by any conventional means, such as with a driver adapted to engage a corresponding recessed socket of the screw.

Figure 5A:
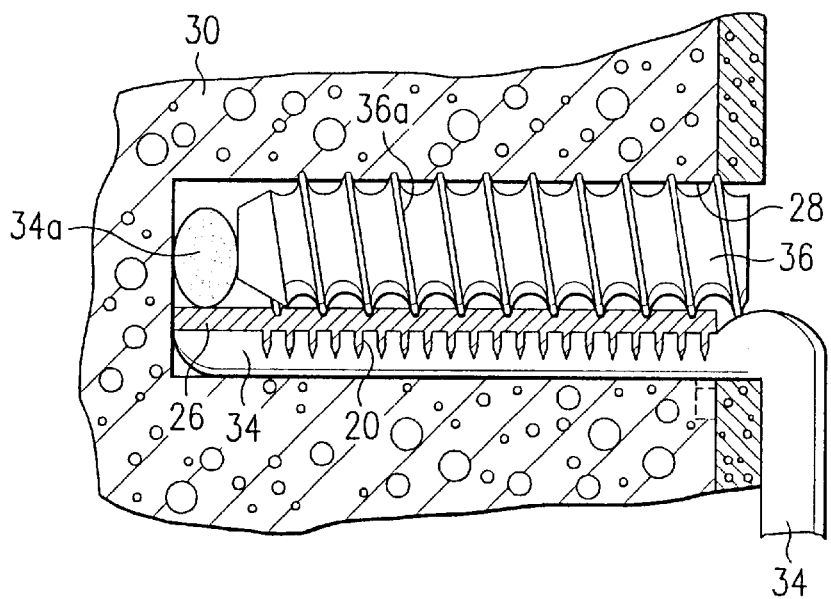
FIG. 5A is a sectional view of the device of FIG. 1 after placement in the patient.
Figure 5B:
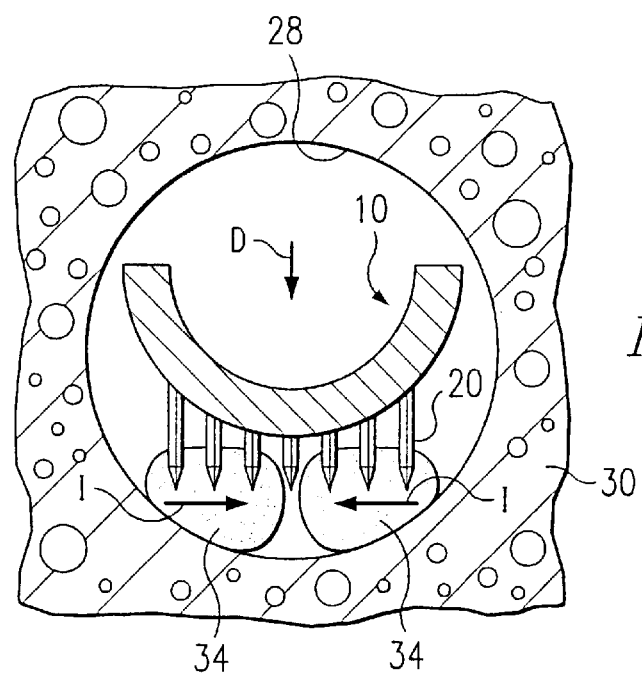
FIG. 5B is a cross sectional view of the device of FIG. 1 during installment in the patient.

Referring now to FIG. 5A, as the screw 36 is rotated, it advances into the bone tunnel 28 via frictional engagement by the threads 36a. The threads 36a engage the grooves 18 of the body portion 12, and also the portion of the bone 30 defining the bone tunnel 28.

As the screw advances, it exerts forces upward into the bone 30, and downward on the device 10, thereby firmly securing the device and graft 34 in the bone tunnel 28. More specifically, in the upward direction, the force produced by the screw 36 causes the threads 36a to sink into the bone 30. Similarly, the downward force on the device 10 causes the spur ends 22a–24a to be driven deeply into the bone 30, thereby further securing the device in the bone tunnel 28. Once engaged with the bone 30, the spurs 22–24 prevent undesirable rotational movement by the device 10 ("rotational migration") that would otherwise be caused by torsional forces associated with the screw's rotation.

The downward force exerted by the screw 36 on the device 10 also causes the spikes 20 to engage and compress the graft 34, thereby biasing the graft in the bone tunnel 28. As the flat plane of spikes 20 engages the graft 34, the graft is held at a number of contact points, the ends 20a, thereby securing the graft in the bone tunnel 28. It can be appreciated that in some circumstances, the ends 20a may be rounded to prevent damage to the graft 34, or sharpened to afford a better purchase on the graft.

Several features of the device help keep the graft 34 centralized under the device 10 while being compressed, and thus prevent graft damage and slippage. First, the spurs 22–24 tend to keep the graft 34 from being squeezed out around the edges of the device 10. Second, referring now to FIG. 5B, it can be appreciated that when the flat plane of spikes 20 compresses the graft 34 downward (indicated by the reference arrow D; screw 36 removed for clarity) into the curved wall of the bone tunnel 28, the graft has less room, and hence experiences greater pressure, at the edges of the flat plane. Thus, if the graft 34 tends to shift laterally in response to the pressure, it will shift inward (indicated by the reference arrows I) to an area of lower pressure, the area corresponding to a more central portion of the device. The central portion of the device 10 has a greater number of adjacent spikes 20, and thus the graft 34 engages more spikes, and hence is better retained.

One advantage of the embodiment described herein is that it securely affixes the graft to the bone, greatly reducing the chance of graft slippage. Another advantage of the embodiment described herein is that the device 10 and the screw 36 are disposed below the surface of the bone 30 in their installed positions. This produces a smooth profile that is less likely to cause the patient discomfort.

Figure 6:
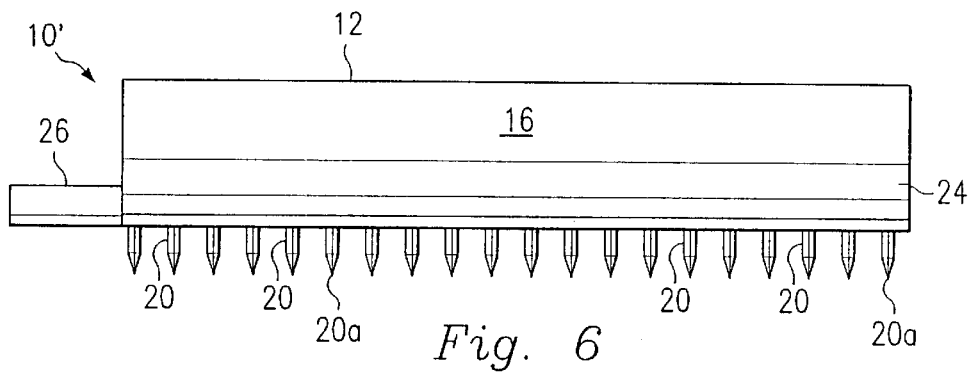
FIG. 6 is a side plan view of a soft tissue fixation device according to another embodiment of the present invention.

Referring to FIG. 6, the reference numeral 10' refers to a soft tissue fixation device according to another embodiment of the invention. This embodiment incorporates several components of the embodiment of FIGS. 1–5B, which are given the same reference numbers. According to FIG. 6, however, the spurs 22–24 of the foregoing embodiment are removed. This embodiment has the advantage of retaining the graft in the bone tunnel without the device invasively engaging the bone, which may benefit certain types of patients.

Figure 7:
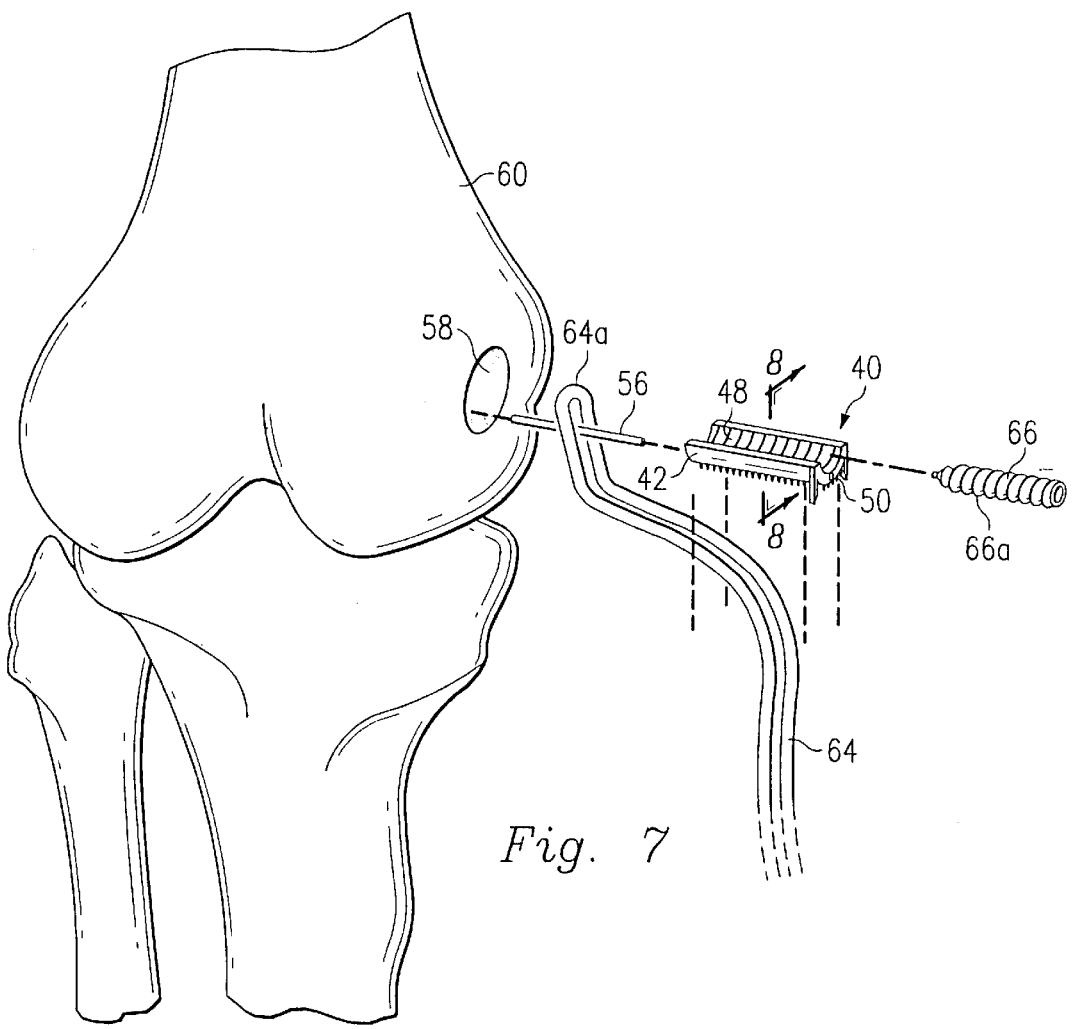
FIG. 7 is a perspective view of a soft tissue fixation device according to yet another embodiment of the present invention being placed in a patient.
Figure 8:
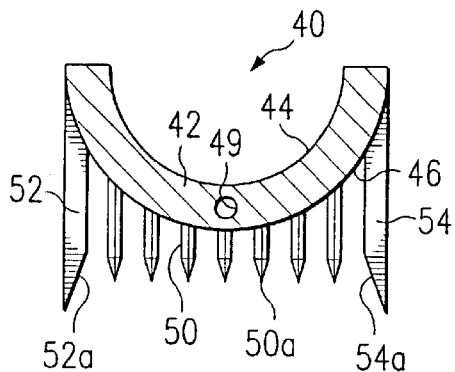
FIG. 8 is a cross sectional view of the device of FIG. 7.
Figure 9:
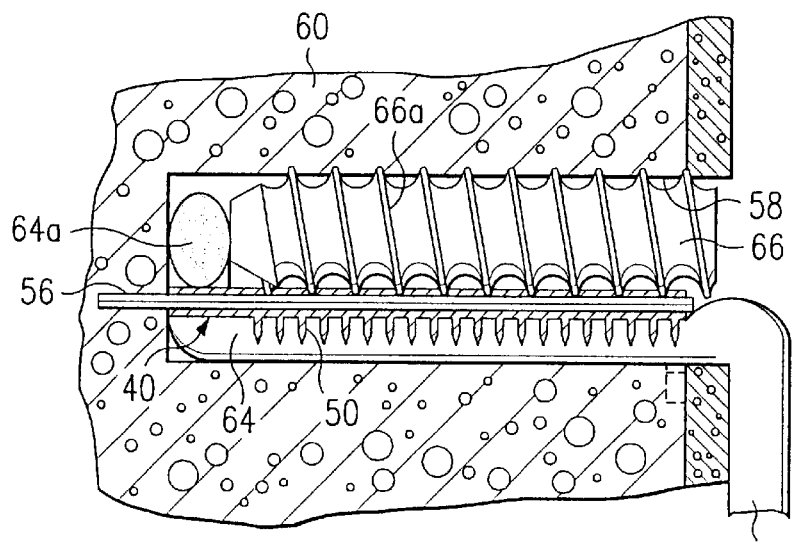
FIG. 9 is a sectional view of the device of FIG. 7 after placement in the patient.

Referring now to FIGS. 7–9, the reference numeral 40 refers to a soft tissue fixation device according to yet another embodiment of the present invention. The device 40 has a semi-cylindrical body portion 42, which is substantially U-shaped in cross-section (FIG. 8).

The body portion 42 has an inner surface 44 and an outer surface 46. A series of grooves 48 are orthogonally disposed along the inner surface 44 of the body portion 42. An axial bore 49 runs the length of the body portion 42, for reasons to be described.

A plurality of spikes 50 protrude from the outer surface 46 of the body portion 42, and extend perpendicular to the longitudinal axis of the body portion 42 and parallel to each other. The distal ends 50a of the spikes 50 define a flat plane extending parallel to an imaginary plane extending between the uppermost surfaces of the body portion 42, as in the previous embodiments. The distal ends 50a of the spikes 50 may be sharpened, as depicted, or rounded.

A pair of spurs 52–54 project from a distal end of the body portion 42 in an orientation parallel to the spikes 50. The spurs 52–54 extend past the flat plane defined by the spike ends 50a, and terminate in chisel-shaped ends 52a–54a, respectively.

A substantially cylindrical guide pin 56 (FIG. 7) is provided for removable disposal in the axial bore 49 of the body portion 42, as will be described.

In operation, a bone tunnel 58 is bored in a patient's bone 60 by any conventional means. In the preferred embodiment, the bone tunnel 58 is bored at a right angle relative to the longitudinal axis of the bone 60, and of a depth slightly greater than the length of the device 40.

The guide pin 56 is installed in the bone tunnel 58 by any conventional means. As shown in FIG. 9, the pin 56 has been driven into the bone 60 to a depth greater than the bone tunnel 58. The guide pin is adapted to be slidably received by the axial bore 49 of the body portion 42.

A graft 64 to be affixed to the bone 60 is bent over itself to form a loop 64a. The graft loop 64a is placed over the distal end of the guide pin 56. The axial bore 49 of the device 40 receives the guide pin 56, and the trailing ends of the graft 64 are threaded under the device and between the spurs 52–54. Thereafter, the device 40, and hence the graft 64, are advanced into the bone tunnel 58, following the guide pin 56.

It is understood that the length of the device 40 inserted in the bone tunnel 58 corresponds directly with the length of graft 64 inserted into the bone tunnel. If the tension on the graft 64 is determined to be less than optimal for the reconstruction procedure, the graft and device 40 may be removed from the bone tunnel 58, and the graft loop 64a re-formed in a position corresponding to producing greater or lesser graft tension, as desired. Thus, the graft tension may be easily adjusted, a significant advantage.

Once proper graft tension has been achieved, an interference screw 66, having threads 66a, is also inserted in the bone tunnel 58 above the device 40 to engage the inner surface 44 of the body portion 42. As is best shown in FIG. 9, as the screw 66 is rotated, it advances into the bone tunnel 58 via the threads 66a's frictional engagement with the grooves 48 of the body portion 42, and the portion of the bone 60 defining the bone tunnel 58. As the screw 66 advances, it exerts forces upward into the bone 60 and downward on the device 40, firmly securing the device and compressing the graft 64 in the bone tunnel 58.

The device 40 enjoys the advantages of the embodiment of FIGS. 1–5B, and also has the benefit of allowing precise placement of the device via the guide pin. Moreover, this embodiment uses both the guide pin and spurs to prevent undesirable rotational migration of the device during tightening of the screw.

Figure 10:
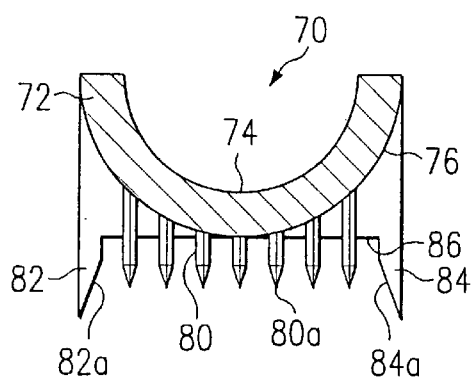
FIG. 10 is a cross sectional view of a soft tissue fixation device according to yet another embodiment of the present invention.

Referring now to FIG. 10, reference numeral 70 refers to a soft tissue fixation device according to yet another embodiment of the invention. This embodiment incorporates the features of either the embodiment of FIGS. 1–5B, or of FIGS. 7–9. According to FIG. 10, however, the spurs of the foregoing embodiments are modified.

The device 70 (FIG. 10) has a semi-cylindrical body portion 72, which is substantially U-shaped in cross-section. The body portion 72 has an inner surface 74 and an outer surface 76. Although not depicted, a series of grooves may be orthogonally disposed along the inner surface 74 of the body portion 72.

A plurality of spikes 80 protrude from the outer surface 76 of the body portion 72. As depicted, the spikes 80 extend perpendicular to the longitudinal axis of the body portion 72, and parallel to each other. The distal ends 80a of the spikes 80 define a flat plane extending parallel to an imaginary plane extending between the uppermost surfaces of the body portion 72. The distal ends 80a of the spikes 80 may be sharpened, as depicted, or rounded. Though not depicted, it is understood that this embodiment has features for retaining a graft loop ("retaining means"), such as a hook, or a suture, or an axially extending integrated pin (e.g., FIG. 1), or a removable guide pin and axial body portion bore (FIG. 7). It is understood that in operation, the device 70 functions in substantially the same manner as the above-described embodiments.

A pair of spurs 82–84 project from a distal end of the body portion 72 in an orientation parallel to the spikes 80. The spurs 82–84 extend past the flat plane defined by the spike ends 80a, and terminate in chisel shaped ends 82a–84a, respectively. The spurs 82–84 are connected by a wall 86, which provides reinforcement against lateral movement by the spurs. The wall 86 stabilizes the spurs, allowing greater penetration of the spur ends 82a–84a into the bone, and thereby further securing the device 70 in the bone tunnel.

It is understood that all spatial references, such as front, rear, upward, and downward, are only for the purposes of explanation of the drawings. This disclosure shows and describes illustrative embodiments, however, the disclosure contemplates a wide range of modifications, changes, and substitutions. For example, the invention encompasses using radial spikes following the contour of the body portion rather than the parallel spikes of the above-described embodiments. Similarly, the flat plane of spike ends may be created by parallel spikes of a uniform length extending from a flattened portion of the body portion. Likewise, variations may employ only some features of the embodiments, such as the spur-less device 10' of FIG. 6, without departing from the scope of the underlying invention. Accordingly, any appropriate construction of the appended claims will reflect the broad scope of the underlying invention.

What is claimed is:

1. A soft tissue fixation device for being biased between a soft tissue graft and an interference screw in a bone tunnel, the device comprising:
   a contoured body portion having an inner surface and an outer surface;
   a plurality of spikes protruding from the outer surface of the body portion, the spikes extending perpendicular to the longitudinal axis of the body portion and parallel to each other, wherein the distal ends of the spikes define a flat plane; and
   a pin axially extending from the body portion for receiving a portion of the graft.

2. The device of claim 1 wherein the pin is permanently affixed to the body portion.

3. The device of claim 1 wherein the pin is a guide pin that is received in an axial bore of the body portion.

4. The device of claim 1 wherein the body portion is substantially U-shaped in cross section.

5. The device of claim 4 further comprising a pair of top surfaces extending between the inner surface and outer surface of the body portion, wherein the flat plane extends parallel to an imaginary plane aligned with the top surfaces.

6. The device of claim 1 further comprising a pair of spurs projecting from a distal end of the body portion in an orientation parallel to the spikes.

7. The device of claim 6 wherein the spurs extend past the flat plane defined by the spike ends, and terminate in chisel-shaped ends.

8. The device of claim 1 further comprising a series of grooves orthogonally disposed along the inner surface of the body portion for engaging threads of the interference screw.

9. The device of claim 1 wherein the distal ends of the spikes are sharpened.

10. The device of claim 1 wherein the distal ends of the spikes are rounded.

11. A soft tissue fixation device for being biased between a soft tissue graft and an interference screw in a bone tunnel, the device comprising:
   a contoured body portion having an inner surface and an outer surface;
   a plurality of spikes protruding from the outer surface of the body portion, the spikes extending perpendicular to the longitudinal axis of the body portion and parallel to each other, wherein the distal ends of the spikes define a flat plane;

a pair of spurs projecting from a distal end of the body portion in an orientation parallel to the spikes; and a pin axially extending from the body portion for receiving a portion of the graft.

12. The device of claim 11 wherein the pin is permanently affixed to the body portion.

13. The device of claim 11 wherein the pin is a guide pin that is received in an axial bore of the body portion.

14. The device of claim 11 wherein the spurs extend past the flat plane defined by the spike ends, and terminate in chisel-shaped ends.

15. The device of claim 11 wherein the body portion is substantially U-shaped in cross section.

16. The device of claim 15 further comprising a pair of top surfaces extending between the inner surface and outer surface of the body portion, wherein the flat plane extends parallel to an imaginary plane aligned with the top surfaces.

17. The device of claim 11 further comprising a series of grooves orthogonally disposed along the inner surface of the body portion.

18. The device of claim 11 wherein the distal ends of the spikes are sharpened.

19. The device of claim 11 wherein the distal ends of the spikes are rounded.

20. A method for attaching a soft tissue graft to a bone, comprising:

forming a tunnel in the bone;

providing a soft tissue fixation device having body portion with a contoured outer surface and a plurality of spikes protruding from the outer surface of the body portion, the spikes extending perpendicular to the longitudinal axis of the body portion and parallel to each other, the distal ends of the spikes defining a flat plane;

attaching the graft to the device;

inserting the device and graft into the bone tunnel;

inserting an interference screw into the bone tunnel above the device; and rotating the screw, thereby biasing the device into place, and thus compressing the graft, such that the graft is retained in the bone tunnel.

21. The method of claim 20 further comprising forming the tunnel in the bone at a right angle to the longitudinal axis of the bone.

22. The method of claim 20 wherein the step of attaching the graft to the device comprises looping the graft over a pin associated with the body portion of the device.

* * * * *